United States Patent [19]
Adachi

[11] Patent Number: 5,080,477
[45] Date of Patent: Jan. 14, 1992

[54] SURFACE TOPOGRAPHER

[76] Inventor: Yoshi Adachi, 16241 Watson Cir., Westminster, Calif. 92683

[21] Appl. No.: 610,774

[22] Filed: Nov. 8, 1990

Related U.S. Application Data

[63] Continuation-in-part of Ser. No. 398,908, Aug. 28, 1989, abandoned.

[51] Int. Cl.$^5$ .............................................. A61B 3/10
[52] U.S. Cl. ................................... 351/212; 351/237; 356/376
[58] Field of Search ............... 351/211, 212, 237, 247; 356/124, 376

[56] References Cited

U.S. PATENT DOCUMENTS

| | | | |
|---|---|---|---|
| 3,169,459 | 2/1965 | Friedberg et al. | 351/212 |
| 4,641,972 | 2/1987 | Haliova et al. | 356/376 |
| 4,692,003 | 9/1987 | Adachi et al. | 351/212 |
| 4,838,682 | 6/1989 | Portnoy | 351/211 |
| 4,863,260 | 9/1989 | Gersten et al. | 351/212 |

Primary Examiner—Rodney B. Bovernick
Assistant Examiner—J. P. Ryan
Attorney, Agent, or Firm—James T. English

[57] ABSTRACT

A computer assisted optical instrument analyzes a differential wave front developed by subtracting the wave front due to a circular grating reticle only in the optical path, from the wave front due to a reflecting surface being analyzed in the optical path including the reticle, to obtain a Foucault shadow fringe pattern indicating the surface curvature. The differential wave front is analyzed by the circular grating and a CCD camera, in polar coordinates, to obtain polynomial coefficients defining the wave front. The polynomial is then plotted and displayed as the topographic shadow fringe pattern of the reflected surface. Dedicated lens and reflector combinations adapt the instrument to specific embodiments in ophthalmology and metrology.

5 Claims, 4 Drawing Sheets

SURFACE TOPOGRAPHER

REFERENCES TO PRIOR APPLICATONS

This application is a continuation-in-part of a prior application for patent on a Surface Topographer, Ser. No. 398,908 filed on 8-28-89, (abandoned).

TECHNICAL FIELD

This invention is related to measuring instruments for the measurement of electromagnetic radiation flux fields for the purpose of inferring characteristics of an illuminated surface, and more particularly to optical and near-optical measurement of physical characteristics of a surface and examining its topography, with special applications in measurement of curvature for ophthalmology, and precision measurement for inspection and manufacturing.

DESCRIPTION OF THE PRIOR ART

A prior patent issued to the same inventor, Adachi, U.S. Pat. No. 4,692,003, teaches the use of real-time analysis of optically generated patterns using circular gratings, and a Moire pattern that indicates transverse aberration from an ideal curvature for an object such as the cornea of a human eye. The invention differs from this patent in that Moire is not used and a different optical system, as well as a different data analysis and processing method using Zernike polynomials, is used. Only the use of the circular grating is common to both.

BRIEF DESCRIPTION OF THE INVENTION

In accordance with the invention, the use of a circular grating reticle in the optical path, lends itself to mathematical identification of points on the wave front, in polar coordinates. A radiated wave front is received by a photometric detector such as a CCD camera, from an illuminated surface through the circular grating reticle, such that the identified points have an intensity value assigned to them. When digitized and processed by a computer and display device, the coordinate and intensity data in the wave front image will produce a shadow fringe pattern if the grating reticle is placed in front of the focus point of the reflective optics, that is, the image of the grating is slightly defocused. The shadow fringe pattern with no reflective surface in the optical path is a series of concentric bands whose number depends on the period (resolution) of the particular grating used. When a surface to be tested is placed in the reflective optical path, the fringes may become distorted and locally spaced further apart in accordance with the contour of the reflective surface. In analyzing curved surfaces such as spheres, one or a series of equally spaced rings are expected for a well formed sphere. The period of the grating reticle establishes the resolution of the analysis; however, interpolation by computer program can display any number of fringes desired for analysis of the topography.

The fundamental teaching of the invention is to analyze the differential wave front; i.e., the perturbed wave front minus (−) the unperturbed wave front at points on a circular grating, to obtain polar coordinate polynomial coefficients from which the surface polynomial equation is constructed. A plot of the polynomial equation reveals the differential shadow fringe pattern indicating any astigmatism; i.e., areas of departure from sphericity if measuring a spherical object, and their location on the sphere.

DETAILED DESCRIPTION OF THE EMBODIMENTS

Figure 1:
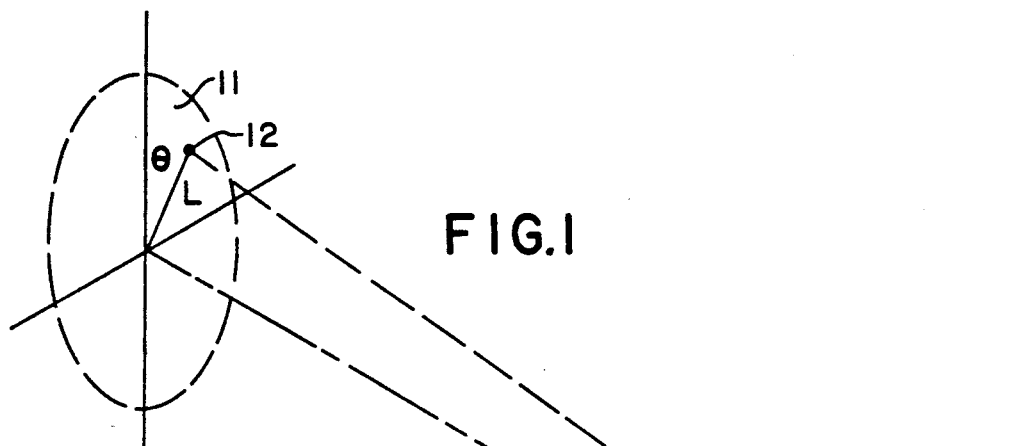
FIG. 1 is an isometric sketch of the mathematical analysis scheme of the invention.
Figure 2:
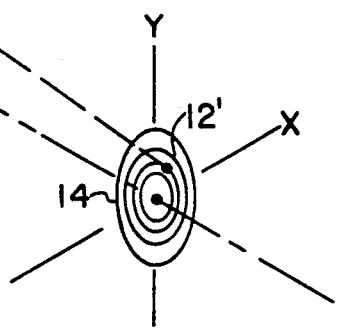
FIG. 2 is an isometric drawing of an embodiment of the invention for measuring cornea curvature or both concave and convex surfaces such as contact lenses.
Figure 2:
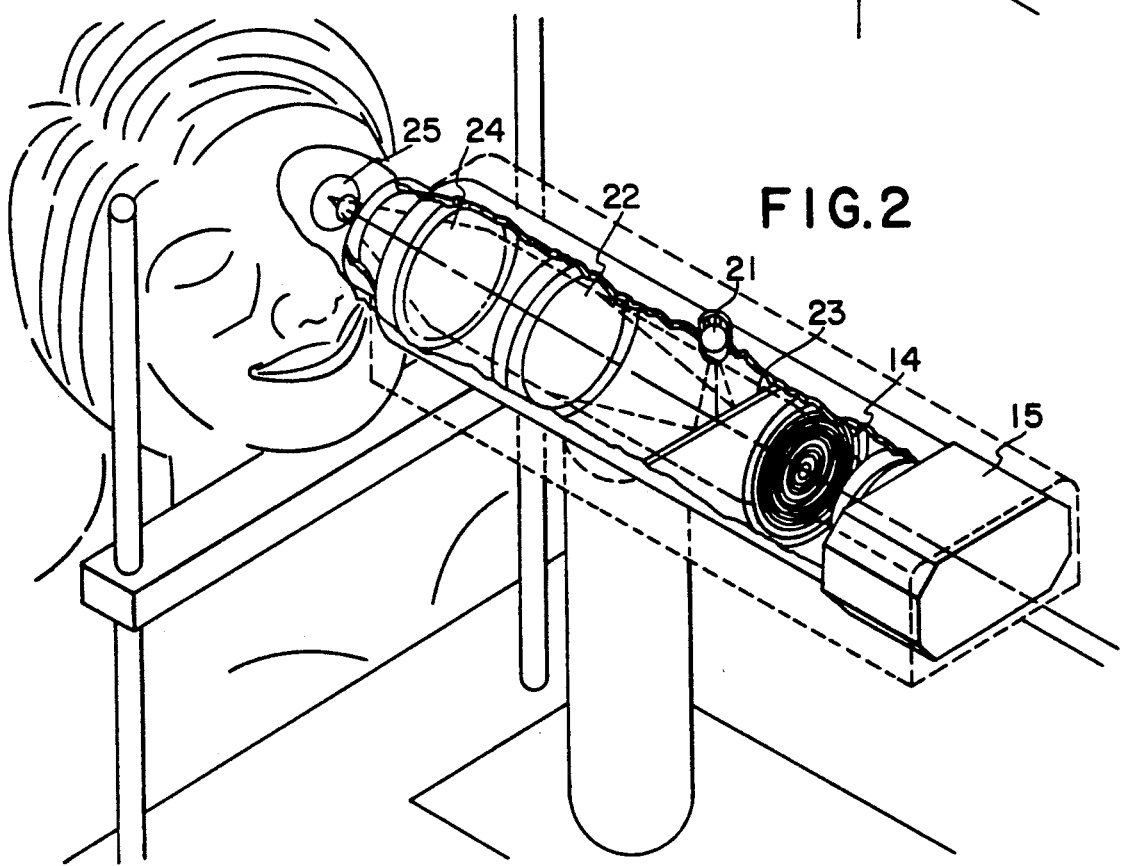

Referring to FIG. 1, we note in the plane of the wave front represented by 11, a point 12 on that wave front, at angle theta ($\theta$), a distance L from the center. This corresponds to the point 12' on the circular grating 14 in the optical path of the wave front 11. It will be noted from FIG. 2 a circular grating such as 14 placed in the optical path of the wave front will identify coordinates of points on the wave front in polar coordinates; i.e., a distance magnitude from center and an angle from vertical, for later computation with the light intensity derived from the Charge Coupled Device (CCD) Camera 15. Thus, the coordinates and intensity of points on the wave front are known for analytical purposes in the embodiment of FIG. 2. In order to analyze the astigmatism or spherical aberration of a convex or a concave surface, the optical scheme of FIG. 2 can be used. The illumination source 21 projects a beam that impinges on a collimating optical lens 22 which outputs a planar wave front, through path compensating optics 24 to the optical surface being analyzed 25. A reflected wave front returns in the opposite direction and is directed through collimating optical lens 22 to a camera 15 through the circular grating 14. The differential wave front is developed at the beamsplitter 23 before presentation to the circular grating. In this way, the polar coordinates of points on the differential wave front are presented to the camera 15 where the intensity of each point is obtained for computation of the differential surface topography or spherical aberration. In operation, the shadow fringe pattern shown in FIG. 3 for example, defining the wave front with only the circular grating reticle in the optical path, will be seen. In a subsequent step, a surface to be tested; for example a concave or a convex lens, is placed in position and a new set of data is recorded. The difference of the wave fronts is computed from the measured coefficients at each point on the circular grating in accordance with the computer program sequence as follows:

Relate the wave front $W(L,\theta)$ to the image coordinate $(x,y)$ $$x = -F\left(\sin\theta \frac{dW}{dL} + \frac{\cos\theta}{L} \frac{dW}{d\theta}\right)$$

$$y = -F\left(\cos\theta \frac{dW}{dL} - \frac{\sin\theta}{L} \frac{dW}{d\theta}\right)$$

where F is the distance from the surface to the beam converging point.

Define the period p.

Let the circular grating be numbered from center to outside by n an integer. The $n^{th}$ circle coordinate will be np.

$$np = x \sin\theta + y \cos\theta$$

$$np = -F\left(\frac{dW}{dL}\right)$$

Generate the wave front polynomial equation.

$$W = K + S11\, L \sin\theta + C11\, L \sin\theta + R20\,(2L^2 - 1) +$$
$$S22\, L^2 \sin 2\theta + C22\, L^2 \cos 2\theta + S31\,(3L^3 - 2L) \sin\theta +$$
$$C31\,(3L^3 - 2L) \cos\theta + R40\,(6L^4 - 6L^2) \ldots$$

Generate the wave front circular grating differential equation.

$$\frac{dW}{dL} = K + S11 \sin\theta + C11 \cos\theta + R20\,(4L) +$$
$$R40\,(24L^3 - 12L) + S22\,(2L) \sin 2\theta + C22\,(2L) \cos 2\theta +$$
$$S31\,(9L^2 - 2) \sin\theta + C31\,(9L^2 - 2) \cos\theta + \ldots$$

Solve:

$$np = -F\left(\frac{dW}{dL}\right) \text{ and}$$

$$\frac{dW}{dL} = K + S11 \sin\theta + C11 \cos\theta + R20\,(4L) +$$
$$R40\,(24L^3 - 12L) + S22\,(2L) \sin 2\theta + C22\,(2L) \cos 2\theta +$$
$$S31\,(9L^2 - 2) \sin\theta + C31\,(9L^2 - 2) \cos\theta + \ldots$$

to obtain ring (Zernike) coefficients S11, C11, R20, etc.
Input the coefficients thus obtained into:

$$W = K + S11\, L \sin\theta + C11\, L \sin\theta + R20\,(2L^2 - 1) +$$
$$S22\, L^2 \sin 2\theta + C22\, L^2 \cos 2\theta + S31\,(3L^3 - 2L) \sin\theta +$$
$$C31\,(3L^3 - 2L) \cos\theta + R40\,(6L^4 - 6L^2) + \ldots$$

which is the wave front.

Compute fringe spacing.

Let Hm be the maximum height of optics; NA is numeric aperture.

$$NA = \frac{Hm}{F} = \sin A \text{ then,}$$

$$\text{Fringe spacing } Fs = \frac{1 - \cos A}{\tan A} \, np$$

np is the number of fringes counted in the pupil of optics under test. Fs may be called equivalent wave length. For wavelength K, the factor Fs/K will be multiplied with the ring coefficients.

Figure 4:
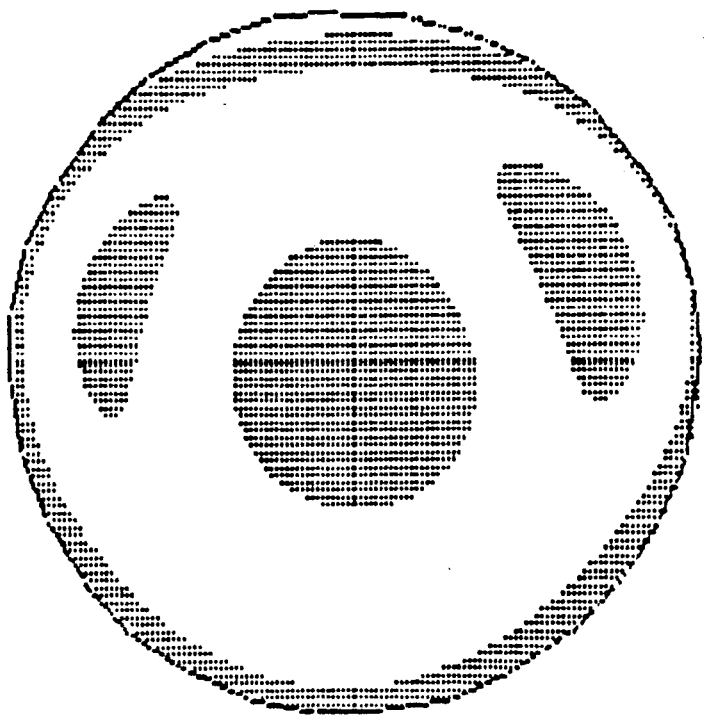
FIG. 4 is a printout of the analysis of the differential pattern observed combining both the circular grating image and the reflected image.

Display the wave front W to image the surface contour, FIG. 4. Note the single fringe and the high degree of symmetry indicating a nearly spherical surface.

The result will be displayed in terms of wave length K of the illumination source.

Figure 3:
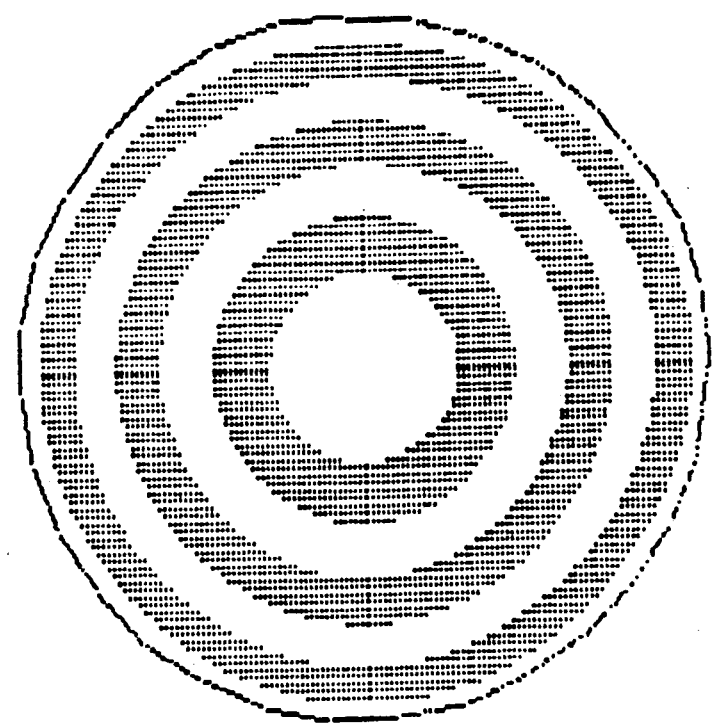
FIG. 3 is a printout of the pattern observed with only the circular grating as a reference.
Figure 5:
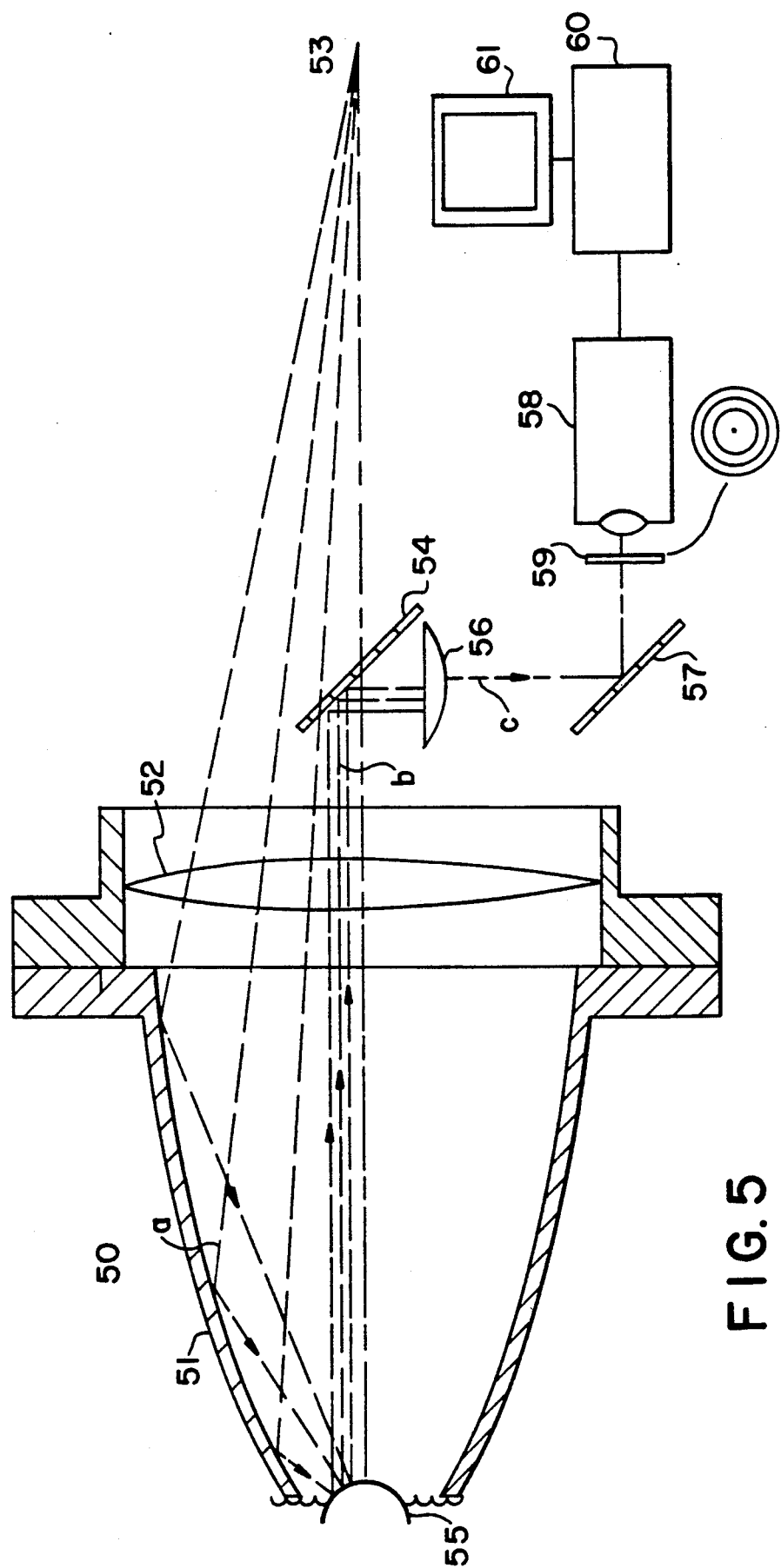
FIG. 5 is a drawing of an embodiment of the invention suitable for measuring convex aspherical surfaces, such as a cornea.
Figure 6:
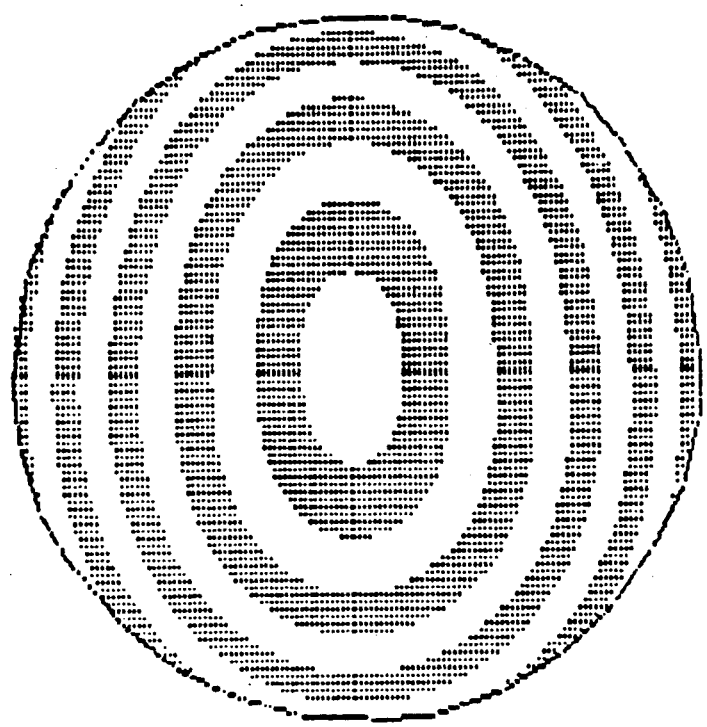
FIG. 6 is a printout of the pattern observed with a calibration model and the circular grating.
Figure 7:
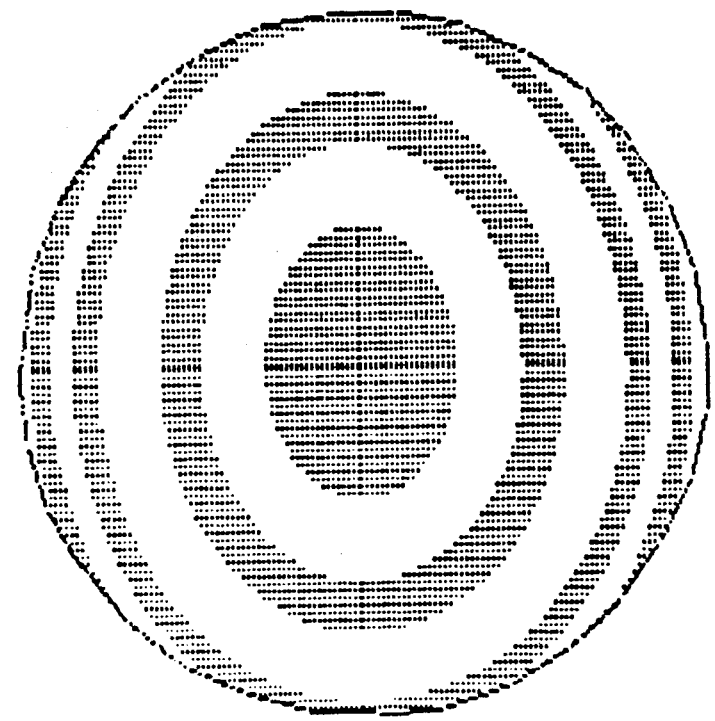
FIG. 7 is a printout of the analysis of the differential pattern observed, combining both the circular grating image and the reflected image.

Referring to FIG. 5 we see an embodiment of the invention directed to measuring curvature of the cornea of the human eye. This keratometer 50 provides an eyepiece 51 which is a parabola having a curvature $X^2 = 2RY$ where $R = 7.7$ millimeters. The eyepiece 51 is placed over the eye such that a point light source 53 is focused by lens 52 to illuminate the parabola 51 and the cornea 55. For example, light ray a is reflected off the wall of the parabola 51 to the cornea and reflected from the cornea through a dichroic mirror 54, through a collimating lens 56, mirror 57, and to the charge coupled device camera 58 through circular grating 59. The output of the camera 58 is in terms of the wave front light intensity at points on the circular grating 59 in polar coordinates. The wave front is computed in computer 60 and displayed on the display device 61 which may be a printer or a CRT. In operation the instrument is calibrated using a standard surface model of a cornea such that the printout of FIG. 6 is obtained. Then the actual test cornea is viewed by the eyepiece 51 and the printout such as FIG. 7 is obtained. This figure shows some degree of toric deformation of the cornea or elongation along the y axis. The fringe pattern of FIG. 3 is normally obtained with no reflective surface or model in the field of view.

Herein have been described the preferred embodiments of the invention. It is recognized that variations, modifications or equivalents will readily occur to those skilled in the art and it is intended that the claims be interpreted as including all such variations, modifications or equivalents.

What is claimed is:

1. A keratometer for measuring the curvature of the cornea of an eye, which comprises:
   means for illuminating an area for receiving said cornea, the area being reflective to said illuminating means;
   means for receiving the reflected illumination wave front from said area;
   a circular grating reticle having spaced rings, said reticle receiving the reflected wave front from the area illuminated by said illuminating means, and transmitting said wavefront therethrough, imparting the image of said reticle rings on said wavefront;
   means for detecting and converting the wave front having the image of said reticle, transmitted through said reticle, to electrical data having ring number from center, and angle from vertical, polar coordinates;
   means for computing the differential illumination of the wave front reflected from the illuminated area through said reticle, from the wave front reflected from the cornea, through said reticle, receiving the electrical data from said means for detecting and converting, said computing means having an output;
   means displaying the differential wave front output of said computing means;

whereby the display images the topography of the cornea as evenly spaced fringes indicating no spherical aberration, or locally unevenly spaced fringes indicating areas of asphericity, in real-time.

2. A keratometer for measuring the curvature of the corneal surface of an eye as described in claim 1 wherein said means for illuminating a surface is a laser diode light source operating in the infrared wavelength region of the electromagnetic spectrum, and said laser diode is operated in a pulsed mode.

3. A keratometer for measuring the curvature of the corneal surface of a human eye as described in claim 1 wherein said means for illuminating a surface comprises:

a parabola having dimensions described by the fomrula $$x^2 = 2R\,y$$

and R is 7.7 millimeters and having a focal point confocal with the cornea focal point.

4. A device for analyzing topography of a surface, which comprises:

means for illuminating an area for receiving said surface, in optical communication therewith;

a circular grating, having spaced rings transmissively receiving the reflected wave front from the area illuminated by said illuminating means;

means for measuring the illumination intensity of the reflected light pattern wave front transmitted through said circular grating, in optical communication with said grating, said means having an output;

means for converting light intensity to electrical output receiving the output of said means for measuring illumination intensity, said converting means having an output;

means for computing light intensity at polar coordinates of said grating from the electrical output of said means for converting, and computing the polynomial defining the wave front; and means displaying the wave front output of said computing means; whereby topography of a surface placed in the illuminated area is displayed as spaced optical fringes indicating the degree of aberration.

5. The method for realtime analysis of corneal curvature which comprises the steps of:

illuminating an area for receiving a corneal surface with wavelengths opaque to said surface, causing a wave front to be reflected from the area;

receiving the wave front in a transmission mode at a circular grating and CCD camera to analyze the flux intensity at points on the wave front in polar coordinates;

computing the cross sectional intensity pattern of the wave front at the circular grating using a polynomial developed from the intensities at the polar coordinates to describe the wave front;

locating the cornea to be measured in the illuminated area;

displaying the intensity pattern with the cornea located in the illuminated area and observing the number of fringes; and computing the distance between fringes at all points to determine asphericity of the cornea.

* * * * *